United States Patent [19]

Iwasaki et al.

[11] Patent Number: 4,888,049
[45] Date of Patent: Dec. 19, 1989

[54] SYNERGIST FOR BIOCIDE

[75] Inventors: Tetsuji Iwasaki; Hitoshi Hosokawa, both of Wakayama, Japan

[73] Assignee: Kao Corporation, Tokyo, Japan

[21] Appl. No.: 56,555

[22] Filed: May 29, 1987

[30] Foreign Application Priority Data

Jun. 27, 1986 [JP] Japan ................... 61-151186

[51] Int. Cl.$^4$ ............................. A01N 43/40
[52] U.S. Cl. ........................... 71/94; 71/86; 71/120; 71/100; 71/DIG. 1; 514/786; 514/567; 514/785; 514/143; 514/483
[58] Field of Search ..................... 71/94, 103

[56] References Cited

U.S. PATENT DOCUMENTS 3,807,983  4/1974  Abramitis ................. 71/66
3,920,443  11/1975  Drewe et al. ............. 71/94
4,075,002  2/1978  Drewe et al. ............. 71/103

Primary Examiner—Glennon H. Hollrah
Assistant Examiner—Amelia A. Owens
Attorney, Agent, or Firm—Flynn, Thiel, Boutell & Tanis

[57] ABSTRACT

A biocide is strengthened in the biocidal effect with a branched guaternary ammonium salt having a group of

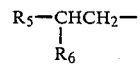

in which R5 is an alkyl or alkenyl having 4 to 18 carbon atoms and R6 is an alkyl or alkenyl having 2 to 16 carbon atoms.

10 Claims, No Drawings

SYNERGIST FOR BIOCIDE

This invention relates to a synergist for a biocide.

Biocides including insecticides, bactericides, herbicides, and plant growth regulators are used in formulations such as emulsions, wettable powders, herbicides, flowable powders, granules, and dust.

It is noted in this connection that various measures are taken in the properties of the formulations so that the principal ingredients contained therein fully exhibit the in activity. However, enhancement in the effects of the biocide cannot be attained by such measures.

Under existing circumstances, where the development of biocides is becoming more and more difficult, enhancing the activity of known biocides is very important.

The present inventors have made extensive and intensive studies to find a specific compound that acts so as to enhance the effect of various biocides. The present invention has been made based on this finding.

A biocide composition of the invention comprises a biocide and a branched quaternary ammonium salt having the formula (I):

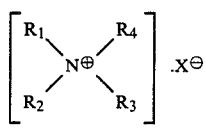
(I)

in which $R_1$, $R_2$ and $R_3$ each are

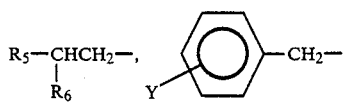

or an alkyl having 1 to 4 carbon atoms, Y being hydrogen or a halogen, $R_5$ is an alkyl or alkenyl having 4 to 18 carbon atoms, $R_6$ is an alkyl or alkenyl having 2 to 16 carbon atoms, at least one of $R_1$, $R_2$ and $R_3$ being

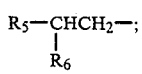

$R_4$ is an alkyl having 1 to 4 carbon atoms or $-CH_2CH_2OH$ and $X^\ominus$ is a counter ion.

The composition preferably comprises 1 part by weight of the biocide and 0.1 to 20, more preferably 0.8 to 20, parts by weight of the quaternary ammonium salt.

The invention further provides a method for strengthening a biocide which comprises using the biocide with a branched quaternary ammonium salt as defined above.

Specifically, in accordance with the present invention, there is provided a synergist for a biocide comprising a branched quaternary ammonium salt represented by the following general formula (I):

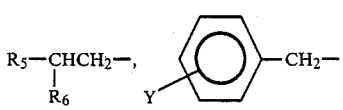

wherein $R_1$, $R_2$, and $R_3$ are each independently

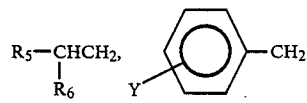

(wherein Y is a hydrogen or halogen atom) or an alkyl group having 1 to 4 carbon atoms, provided that at least one of them is

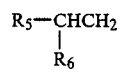

where $R_5$ is an alkyl or alkenyl group having 4 to 18 carbon atoms; $R_6$ is an alkyl or alkenyl group having 2 to 16 carbon atoms; $R_4$ is an alkyl group having 1 to 4 carbon atoms or $-CH_2CH_2OH$; and $X^\ominus$ is a counter anion.

Although the counter anion $X^\ominus$ in the general formula (I) is not particularly limited, examples of preferable counter anion include $CH_3SO_4$, halogen atoms (e.g., Cl, Br, and I), $C_2H_5SO_4$, $HO(CH_2)_mCOO$ (wherein m is an integer of 1 to 5),

(wherein R is an alkyl group having 1 to 3 carbon atoms), and

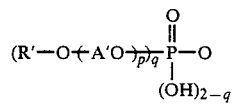

(wherein R' is an alkyl or alkenyl group having 8 to 22 carbon atoms, A' is an alkylene group having 2 to 4 carbon atoms, p is an integer of 0 to 20, and q is 1 or 2).

The compound represented by the general formula (I) can be produced by known methods. For example, it can be produced by quaternizing a tertiary amine represented by the following general formula (II) with a quaternizing agent such as methyl chloride, methyl bromide or dimethyl sulfate:

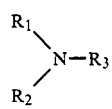
(II)

wherein $R_1$, $R_2$, and $R_3$ are as defined above with respect to formula (I).

The tertiary amine represented by formula (II) can also be produced by known methods. For example, it can be produced by directly aminating an alcohol represented by the following general formula (III) with ammonia, methylamine, or dimethylamine:

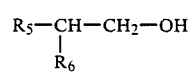
(III)

wherein $R_5$ and $R_6$ are as defined above with respect to formula (I).

Preferable compounds among the compounds represented by the general formula (I) are those represented by the following formulae (IV) to (VI):

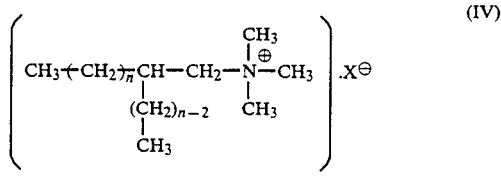

wherein n is an integer of 3 to 17 and X is Cl, Br or $CH_3SO_4$;

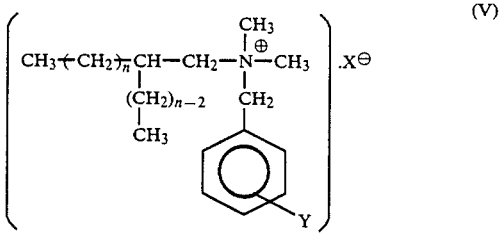

wherein n is an integer of 3 to 17, Y is a hydrogen or halogen atom, and X is Cl, Br or $CH_3SO_4$; and

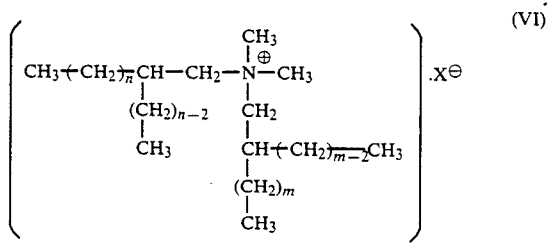

wherein n and m are each independently an integer of 3 to 17 and X is Cl, Br or $CH_3SO_4$. Among them the compounds represented by formula (IV) are particularly preferable.

The synergist for a biocide is characterized in that it has a branched alkyl group as opposed to conventional synergists which have a straight-chain alkyl group or a straight-chain alkenyl group.

Because of its structure, the synergist for a biocide of the present invention is not only free from phytotoxicity when it is used in combination with the biocide, it also can enhance by twice to thrice the effect of the biocide.

The synergist for a biocide of the present invention is used in an amount of usually 0.1 to 5, preferably 0.2 to 4 in terms of a weight ratio relative to the principal ingredient of the biocide.

The form of the preparation is not limited and may be any of an emulsion, flowable powder, wettable powder, dust, etc. Therefore, other additives such as emulsifiers, dispersants or carriers can be added according to the preparation.

The synergist of the present invention can be used by incorporating it in the above-mentioned various preparations or by adding it to the above-mentioned preparations when they are diluted for use. The synergism can be attained by either of the above-mentioned methods.

Although the reason why the synergist for a biocide of the present invention exhibits such a remarkable synergistic activity is not yet fully understood, it is believed that the synergist for a biocide of the present invention breaks the wax layer present on the surface of a plant and the wax present on an insect, thereby promoting the penetration of the biocide into the plant, insect and bacterium regardless of the structure of the biocide.

In view of the above, it is preferred that the synergist for a biocide of the present invention be used at 50 ppm or higher in terms of its concentration in a diluted state.

Examples of the biocide for which the synergist of the present invention may be used will now be described, though the biocides are not limited to them. Further, it should be noted in this connection that the synergist of the present invention can be safely used for various crops without exhibiting phytotoxicity. Examples of the insecticide include pyrethroid insecticides such as fenvalerate (α-cyano-3-phenoxybenzyl 2-(4-chlorophenyl)-3-methyl-valerate) and Baythroid (cyano(4-fluoro-3-phenoxyphenylmethyl-3-(2,2-dichloroethenyl)-2,2-dimethylcyclopropanecarboxylate); organophosphorus insecticides such as DDVP (2,2-dichlorovinyl dimethyl phosphate), Sumithion (dimethyl 4-nitro-m-tolyl phosphorothionate), Malathon (S-(1,2-bis(ethoxycarbonyl)ethyl) dimethyl phosphorothiolothionate), dimethoate (dimethyl S-(N-methylcarbamoylmethyl) phosphorothiolothionate), Elsan (S-(α-(ethoxycarbonyl)benzyl) dimethyl phosphorothiolothionate), and Baycide (0,0-dimethyl 0-(3-methyl-4-methylmercaptophenyl) thiophosphate); carbamate insecticides such as Bassa (o-butylphenyl methylcarbamate), MTMC (m-tolylmethylcarbamate), Meobal (3,4-dimethylphenyl N-methylcarbamate), NAC (1-naphthyl N-methylcarbamate); methomyl (methyl N-((methylcarbamoyl)oxy)thioacetimidate); and cartap (1,3-bis(carbamoylthio)-2-(N,N-dimethylamino)-propane hydrochloride).

Examples of the acarcide include Smite (2-(2-p-tert-butylphenoxy)isopropoxy)isopropyl 2-chloroethyl sulfide), Acricid (2,4-dinitro-6-sec-butylphenyl dimethylacrylate), Chlormite (isopropyl 4,4-dichlorobenzilate), Akar (ethyl 4,4-dichlorobenzilate), Kelthane (1,1-bis(p-chlorophenyl)-2,2,2-trichloro)ethanol, Citrazon (ethyl O-benzoyl-3-chloro-2,6-dimethoxybenzohydroxamate), Plictran (tricyclohexyltin hydroxide), and Omite (2-(p-tert-butylphenoxy)cyclohexyl 2-propynyl sulfite).

Examples of the bactericide include organosulfur bactericides such as Dithane (zinc ethylenebis(dithiocarbamate), maneb (manganese ethylenebis(dithiocarbamate), and thiram (bis(dimethylthiocarbamoyl) disulfide); Benlate (methyl 1-(butylcarbamoyl)-2-benzimidazolecarbamate); Difolatan (N-tetrachloroethylthio-4-cyclohexene-1,2-dicarboximide); Daconil (tetrachloroisophthalonitrile); Pansoil (5-ethoxy-3-trichloromethyl-1,2,4-thiadiazole); thiophanate-methyl(1,2-bis(3-methoxycarbonyl-2-thioureido)benzene); Rabcide (4,5,6,7-tetrachlorophthalide), Kitazin-P (0,0-diisopropyl S-benzyl phosphorothiolate); Hinosan (o-ethyl diphenyl phosphorodithiolate); and probenazole (3-allyloxy-1,2-benzothiazole 1,1-dioxide).

Examples of the herbicide include Stam (3',4'-dichloropropionanilide), Saturn (S-4-chlorobenzyl N,N-diethylthiolcarbamate), DCMU (3-(3,4-dichlorophenyl)-1,1-dimethylurea), and Gramoxone (1,1'-dimethyl-4,4'-bipyridinium dichloride).

Examples of the plant growth regulator include MH (maleic hydrazide) and Ethrel (2-chloroethylphosphonic acid).

EXAMPLES

The synergist for a biocide of the present invention will now be described in more detail with reference to the following examples which should not be construed as limiting the scope of the present invention.

Synergist for a biocide

Compound 1 according to the present invention

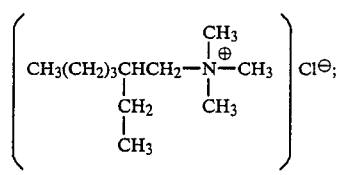

Compound 2 according to the present invention

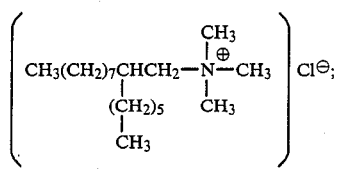

Compound 3 according to the present invention

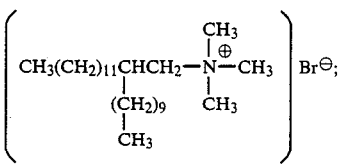

Compound 4 according to the present invention

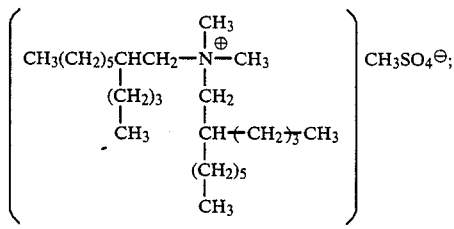

Compound 5 according to the present invention

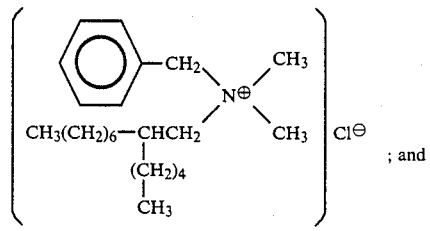

Compound 6 according to the present invention

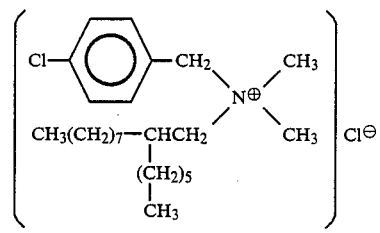

EXAMPLE 1

Paraquat herbicide

| (Formulation No. 1) | | |
|---|---|---|
| Paraquat | 24% | (on the weight basis; the same shall apply hereinafter) |
| compound No. 1 according to the present invention | 20% | |
| water | 56% | |
| (Comparative formulation No. 1) | | |
| paraquat | 24% | |
| polyoxyethylene alkylamine | 20% | |
| water | 56% | |

Crabgrasses (30 crabgrasses per pot) which were in a trifoliate stage were treated with the above herbicide in a predetermined concentration. 7 days after the treatment, the weight of survival at the aerical part and the percentage herbicidal effect relative to the untreated section (%) were calculated. 50% herbicidal concentration was also determined. The results are shown in Table 1.

TABLE 1

| Active ingredient concn. | Formul. No. 1 | Comp. formul. No. 1 |
|---|---|---|
| herbicidal effect (%) | | |
| 2000 ppm | 100 | 96 |
| 1000 | 90 | 82 |
| 500 | 81 | 60 |
| 250 | 58 | 38 |
| 125 | 41 | 13 |
| 50% herbicidal concn. (ppm) | 190 | 385 |

EXAMPLE 2

Kelthane acaricide

| (Formulation No. 2) | |
|---|---|
| Kelthane | 40% |
| xylene | 30% |
| compound 2 according to the present invention | 20% |
| emulsifier 2* | 10% |
| (Comparative Formulation No. 2) | |
| Kelthane | 40% |
| xylene | 30% |
| lauryldimethyl-ammonium chloride | 20% |
| emulsifier 2 | 10% |
| *emulsifier 2 | |
| alkylbenzenesulfonate | 30% |
| polyoxyethylene(15) nonylphenol ether | 30% |
| polyoxyethylene(20) | 40% | oleyl ether

Female two-spotted spider mite imagoes were inoculated with 30 imagoes per section in the three-course system and incubated at 25° C. for 24 hr. Thereafter, the acaricidal effect was assayed by the leaf dipping method. The percentage acaricidal effect relative to an untreated section was determined 24 hr after the treatment with the acaricide. Further, the median lethal concentration was also determined. The results are shown in Table 2.

TABLE 2

| Active ingredient concn. | Formul. No. 2 | Comp. formul. No. 2 |
|---|---|---|
| acaricidal effect (%) | | |
| 500 ppm | 100 | 68 |
| 250 | 88 | 45 |
| 125 | 72 | 28 |
| 62.5 | 48 | 11 |
| $LC_{50}$ concn. (ppm) | 70 | 300 |

EXAMPLE 3

Sumithion insecticide

| (Formulation No. 3) | |
|---|---|
| Sumithion | 55% |
| xylene | 15% |
| compound 3 according to the present invention | 20% |
| emulsifier 3* | 10% |
| (Comparative Formulation No. 3) | |
| Sumithion | 55% |
| xylene | 35% |
| emulsifier 4* | 10% |
| *emulsifier 3 | |
| alkylbenzenesulfonate | 30% |
| polyoxyethylene(11) nonylphenyl ether | 15% |
| polyoxyethylene(20) styrenated phenol ether | 55% |
| *emulsifier 4 | |
| alkylbenzenesulfonate | 30% |
| polyoxyethylene(11) nonylphenyl ether | 30% |
| polyoxyethylene(20) styrenated phenol ether | 40% |

Third-instar rice insect larvae were incubated. Thereafter, the insecticidal effect of the insecticide was assayed by the leaf dipping method using 10 larvae per section in the three-course system. The percentage insecticidal effect relative to an untreated section was determined 24 hr after the treatment. Further, the median lethal concentration was also determined. The results are shown in Table 3.

TABLE 3

| Active ingredient concn. | Formul. No. 3 | Comp. formul. No. 3 |
|---|---|---|
| insecticidal effect (%) | | |
| 100 ppm | 92 | 55 |
| 75 | 80 | 30 |
| 50 | 63 | 21 |
| 25 | 41 | 10 |
| $LC_{50}$ concn. (ppm) | 35 | 95 |

EXAMPLE 4

Thiophanate-methyl bactericide

| (Formulation No. 4) | |
|---|---|
| thiophanate-methyl | 50% |
| clay | 25% |
| compound 4 according to the present invention | 20% |
| dispersant 1* | 5% |
| (Comparative Formulation No. 4) | |
| thiophanate-methyl | 50% |
| clay | 45% |
| dispersant 1* | 5% |
| *dispersant 1 | |
| sodium sulfate of a condensate of naphthalene with formalin | 60% |
| sodium lauryl sulfate | 40% |

The above bactericide was applied to cucumbers which were in a pentafoliate stage. 3 days after the application, the leaves of the cucumbers were cut out and used for tests. Anthrax bacilli were previously incubated in a Petri dish and the agar medium was perforated with a cork borer to form bacillus-containing agar medium. This medium was placed on the center of the leaf which had been cut out, followed by incubation in a Petri dish for 4 days. Thereafter, the extent of spreading of the spot accompanying the disease was determined, and the protective value relative to an untreated section (%) was calculated. Further, the 50% control concentration was also determined. The results are shown in Table 4.

TABLE 4

| Active ingredient concn. | Formul. No. 4 | Comp. formul. No. 4 |
|---|---|---|
| protective value (%) | | |
| 1000 ppm | 100 | 90 |
| 500 | 93 | 71 |
| 250 | 78 | 54 |
| 125 | 55 | 32 |
| 62.5 | 30 | 11 |
| 50% control concn. (ppm) | 110 | 225 |

EXAMPLE 5

Maleic hydrazide auxillary bud inhibitor

| (Formulation No. 5) | |
|---|---|
| potassium salt of maleic hydrazide | 22% |
| compound 5 according to the present invention | 25% |
| water | 53% |
| (Comparative Formulation No. 5) | |
| potassium salt of maleic hydrazide | 22% |
| laurylbenzyldimethylammonium chloride | 25% |
| water | 53% |

Tabacco belonging to the species Virginia was cultivated in a 4-"sun" (4.772-in.) flowerpot. When tabacco was in 50% bloom, it was subjected to topping. Immediately after the topping, the above auxillary bud inhibitor having a predetermined concentration was applied. The tabacco was left as it was for 14 days. Thereafter, the weight of survival of the auxillary buds was determined in order to calculate the percentage auxillary bud inhibiting effect relative to an untreated section. The results are shown in Table 5.

TABLE 5

| Active ingredient concn. | Formul. No. 5 | Comp. formul. No. 5 |
|---|---|---|
| axillary bud inhibiting effect (%) | | |
| 600 ppm | 95 | 77 |
| 300 | 85 | 50 |
| 150 | 63 | 41 |
| 75 | 43 | 10 |
| 50% axillary bud inhibition concn. (ppm) | 105 | 300 |

Example 6

Karmex D herbicide:

| (Formulation No. 4) | |
|---|---|
| DCMU | 50% |
| clay | 46% |
| dispersant 2* | 4% |
| *dispersant 2 | |
| sodium sulfate of a condensate of naphthalene with formalin | 50% |
| sodium lauryl sulfate | 50% |

The above-mentioned preparation was diluted with water to have a predetermined concentration. Subsequently the compound 6 according to the present invention was added to the resulting diluted solution so that the concentration of the compound is 2000 ppm. The herbicidal effect of the resulting liquid herbicide was assayed in the same manner as in Example 1. The results are shown in Table 6.

TABLE 6

| Active ingredient concn. | Section to which compound 6 of the present invention has been added | unadded section |
|---|---|---|
| herbicidal effect (%) | | |
| 2000 ppm | 100 | 95 |
| 1000 | 91 | 82 |
| 500 | 77 | 63 |
| 250 | 55 | 40 |
| 125 | 39 | 11 |
| 50% herbicidal concn. (ppm) | 210 | 380 |

What is claimed is:

1. A biocide composition which comprises a biocide and a branched quaternary ammonium salt having the formula (I):

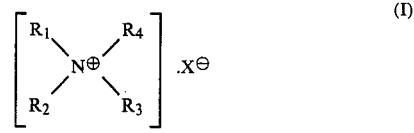

in which $R_1$, $R_2$ and $R_3$ each are

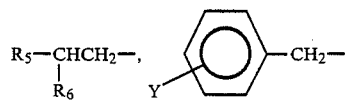

or an alkyl having 1 to 4 carbon atoms, Y being hydrogen or a halogen, $R_5$ being an alkyl or alkenyl having 4 to 18 carbon atoms, $R_6$ being an alkyl or alkenyl having 2 to 16 carbon atoms, at least one of $R_1$, $R_2$ and $R_3$ being

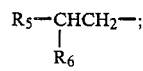

$R_4$ is an alkyl having 1 to 4 carbon atoms or $-CH_2C-H_2OH$ and $X^\ominus$ is a counter ion.

2. The biocide composition as claimed in claim 1, which comprises 1 part by weight of the biocide and 0.1 to 20 parts by weight of the quaternary ammonium salt.

3. The biocide composition as claimed in claim 1, which comprises 1 part by weight of the biocide and 0.8 to 20 parts by weight of the quaternary ammonium salt.

4. A method for strengthening a biocide which comprises using the biocide with a branched quaternary ammonium salt as defined in claim 1.

5. The biocide composition as claimed in claim 1, wherein said biocide is paraquat.

6. The biocide composition as claimed in claim 1, wherein said branched quaternary ammonium salt is 2-hexyldecyl-trimethyl ammonium chloride.

7. A biocide composition which comprises paraquat and 2-hexyldecyl-trimethyl ammonium chloride.

8. A biocide composition consisting of paraquat and 2-hexyldecyl-trimethyl ammonium chloride.

9. The biocide composition as claimed in claim 1, wherein said biocide is a herbicide.

10. A biocide composition which comprises a biocide and 2-n-butyl-n-octyl-trimethyl ammonium chloride.

* * * * *